United States Patent [19]

Clar

[11] Patent Number: 5,055,040
[45] Date of Patent: Oct. 8, 1991

[54] TOOTH SHADE SELECTION USING A NEW COMPARATOR

[76] Inventor: Milton Clar, 11801 Rockville Pike, Apt. #705, Rockville, Md. 20852

[21] Appl. No.: 446,727

[22] Filed: Dec. 6, 1989

[51] Int. Cl.[5] .................. A61C 19/10; A61C 1/00; A61C 3/00; A61C 5/00
[52] U.S. Cl. ............................. 433/26; 433/29; 433/215
[58] Field of Search ............ 356/423; 128/630; 430/357; 433/26, 29, 215

[56] References Cited

U.S. PATENT DOCUMENTS

| | | | |
|---|---|---|---|
| 1,601,616 | 9/1926 | Friese-Greene | 430/357 |
| 3,436,157 | 5/1966 | Adler et al. | 433/26 |
| 4,618,325 | 10/1986 | Appelle | 433/26 |

Primary Examiner—John J. Wilson
Assistant Examiner—Cindy A. Cherichetti
Attorney, Agent, or Firm—Shapiro and Shapiro

[57] ABSTRACT

A tooth shade comparator comprises a viewing tube having a removable base at one end thereof and having an eyepiece at the opposite end thereof. The base is constructed for placement over a tooth in the mouth of a patient and has an opening for exposing the tooth to the interior of the viewing tube while excluding ambient light from the tooth. The base also has a slit for receiving a shade guide element that is placed side by side with the patient's tooth. The tooth and the shade guide element are illuminated by an electric lamp through an opening in the side wall of the tube. The eyepiece includes a lens that provides a magnified image of the tooth and the shade guide element. Half tone filters may be inserted in a light path between the shade guide element and the eyepiece. A set of removable bases having different arrangements of openings and slits provides versatility for shade comparison with different teeth.

19 Claims, 1 Drawing Sheet

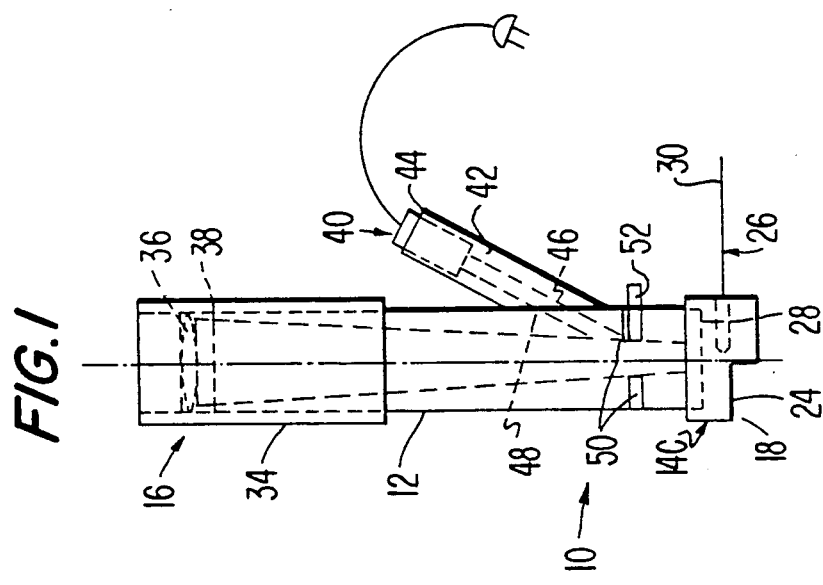
FIG. 1
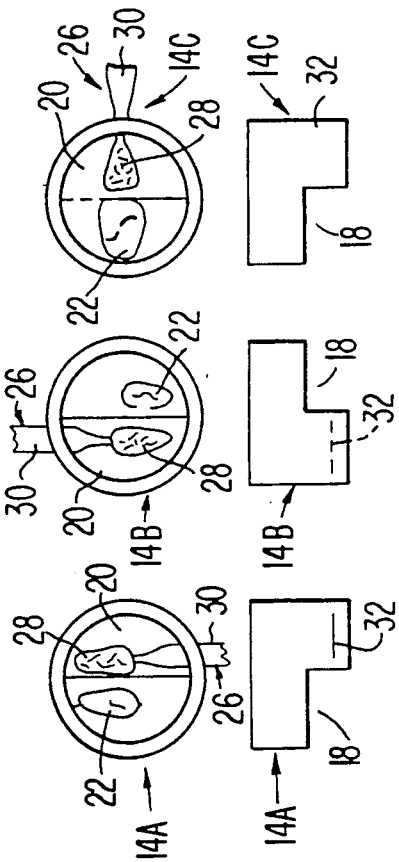
FIG. 2A  FIG. 2B  FIG. 2C
FIG. 3A  FIG. 3B  FIG. 3C
FIG. 4  FIG. 5

TOOTH SHADE SELECTION USING A NEW COMPARATOR

BACKGROUND OF THE INVENTION

This invention is concerned with the selection of prosthetic tooth colors and is more particularly concerned with an improved tooth shade comparator.

Selection of an appropriate color or shade for teeth of prosthetic devices involves color comparison of patients' teeth with shade guide elements. To make this comparison, a dentist places a selected shade guide element adjacent to a patient's tooth and attempts to determine whether there is a color match. The shade guide element may be one of a set of artificial teeth of different colors mounted on metal strips.

Despite the best efforts of dentists to select a prosthetic tooth color that matches the color of a patient's tooth, errors in color selection are common. When a patient rejects a dental prosthesis because the artificial teeth do not match the color of the patient's teeth, there may be significant financial loss to the dentist and/or the dental laboratory that manufactured the prosthesis, and the dentist's competence may be questioned. At the very least, there is the inconvenience of having to manufacture a new prosthesis.

BRIEF DESCRIPTION OF THE INVENTION

The present invention provides a simple, yet highly effective solution to the problem of incorrect selection of the shade of prosthetic teeth. The invention is based upon the premise that a principal factor in improper shade selection is the effect of ambient light. In accordance with the invention, a color comparison is made while a patient's tooth and a shade guide element, arranged side by side, are isolated from ambient light and are illuminated with a dedicated light source.

In accordance with one of the broader aspects of the invention, a tooth shade comparator comprises a viewing tube with a base at one end of the tube shaped for placement in the mouth of a patient over the patient's tooth, the base having an opening to expose the patient's tooth to the interior of the tube and having means for receiving a shade guide element therein adjacent to the patient's tooth, said base and said tube being constructed substantially to isolate said tooth and said shade guide element from ambient light, and a light source mounted on the tube and constructed to illuminate the patient's tooth and the adjacent shade guide element for viewing through the tube from an opposite end of the tube.

In accordance with another of the broader aspects of the invention, a method of comparing color of a tooth in a patient's mouth with color of a shade guide element comprises placing one end of a viewing tube over the tooth in a manner that substantially excludes ambient light from the tooth while exposing the tooth to the interior of the tube, placing the shade guide element adjacent to the tooth in a manner that substantially excludes ambient light from the shade guide element, illuminating the tooth and the shade guide element internally of the tube, and viewing the tooth and the shade guide element through the tube from an opposite end thereof.

BRIEF DESCRIPTION OF THE FIGURES OF THE DRAWINGS

The invention will be further described in conjunction with the accompanying drawings, wherein:

FIG. 1 is a side elevation view of a tooth shade comparator in accordance with the invention;

FIGS. 2A, 2B, and 2C are side elevation views of a set of bases that may be employed in the invention;

FIGS. 3A, 3B, and 3C are end views corresponding to FIGS. 2A, 2B, and 2C, respectively, and showing different arrangements of patient's teeth and shade guide elements;

FIG. 4 is a plan view of a filter that may be employed in the invention; and

FIG. 5 is a side edge view of the filter.

DESCRIPTION OF PREFERRED EMBODIMENTS OF THE INVENTION

As shown in FIG. 1, a tooth shade comparator 10 in accordance with the invention comprises a viewing tube 12, such as a stainless steel cylinder, having a base 14C at one end and an eyepiece 16 at the opposite end. The base is preferably one of a set of removable bases 14A-C, a typical set being shown in FIGS. 2A-C and 3A-C. In the preferred form, the base is a cup-shaped cap formed of flexible silicone material and having a friction fit with one end of the tube that is inserted into the base. Since the bases are removable, they may be readily sterilized and replaced when necessary.

In the preferred form, the base has an external step 18 and an internal step 20. An opening 22 is provided through a surface 24 of the external step closest to the end of the viewing tube, the opening being shaped to expose the patient's tooth to the interior of the viewing tube while the patient's tooth is substantially isolated from ambient light. The internal step is complementary to the external step and provides a space for receiving a shade guide element 26 (commonly referred to as a shade guide tab) selected from a multi-hued set. The shade guide element may comprise an artificial tooth 28 mounted on the end of a metal strip 30 and is inserted into the base through a slit 32 in the side wall of the base. As is apparent in FIGS. 2A-C and 3A-C, different arrangements of openings and slits may be provided in the members of the set of bases to facilitate color comparison with different teeth in the patient's mouth.

The eyepiece comprises a tube 34, such as a stainless steel cylinder, that is friction fit over the end of the viewing tube remote from the base and that contains a magnifying lens 36 mounted adjacent to an internal stop 38. For focusing of a magnified optical image of a patient's tooth and an adjacent shade guide element, the eyepiece is moved along the length of the viewing tube.

A dedicated light source 40 is provided in a tubular arm 42 mounted on the viewing tube. The light source has a socket 44 adapted to be connected to a low voltage power supply and to receive an electric lamp 46, preferably a 5000 Kelvin halogen lamp, for illuminating a patient's tooth and an adjacent shade guide element through an opening 48 in the side wall of the viewing tube. For this purpose, the arm is angulated relative to the viewing tube as shown in FIG. 1.

The side wall of the viewing tube is preferably provided with slots 50 through which selected half tone color filters 52 (FIGS. 4 and 5) may be inserted into a light path between a shade guide element and the eyepiece. Filters are not placed in the light path between the patient's tooth and the eyepiece. Suitable filter colors include yellow, gray, reddish brown, and reddish gray.

To use the tooth shade comparator of the invention, a shade guide element having a shade deemed to be close to the color of a patient's tooth is inserted through a slit in a base, as shown in FIGS. 3A–C; the base is placed on the end of the viewing tube and is also placed over the patient's tooth; and with the light source energized and the eyepiece adjusted to provide a focused magnified image of the patient's tooth and the adjacent shade guide element, a color comparison is made. Different shade guide elements may be inserted into the base to determine a best match with the color of the patient's tooth, and if necessary, filters may be inserted until a close color match is obtained. By virtue of the invention, an accurate color match is obtained simply and effectively.

While preferred embodiments of the invention have been shown and described, it will be apparent to those skilled in the art that changes can be made in these embodiments without departing from the principles and spirit of the invention, the scope of which is defined in the appended claims.

The invention claimed is:

1. A tooth shade comparator comprising a viewing tube with a base at one end of the tube shaped for placement in the mouth of a patient over the patient's tooth, said base having an opening for exposing the patient's tooth to the interior of the tube and having means for receiving a shade guide element therein adjacent to the patient's tooth, said base and said tube being constructed substantially to isolate said tooth and said shade guide element from ambient light, and a light source mounted on said tube and constructed to illuminate the patient's tooth and the adjacent shade guide element for viewing through the tube from a opposite end of the tube.

2. A tooth shade comparator in accordance with claim 1, wherein said base comprises a cap removably mounted on said one end of said tube.

3. A tooth shade comparator in accordance with claim 2, wherein said cap is formed of flexible material and has a friction fit with said one end of said tube.

4. A tooth shade comparator in accordance with claim 2, wherein said cap has an external step for receiving the patient's tooth, said opening being formed in a surface of said step adjacent to said one end of said tube, and wherein said cap has an internal step complementary to said external step providing a space internally of said cap for receiving said shade guide element adjacent to said tooth.

5. A tooth shade comparator in accordance with claim 4, wherein said cap has a slit in a side wall of the cap through which said shade guide element is inserted into said space.

6. A tooth shade comparator in accordance with claim 4, wherein said cap is one of a set of caps, each mountable on said one end of said tube, the caps of said set having different arrangements of openings and slits to facilitate placement of the cap over different teeth in the patient's mouth and to permit the insertion of shade guide elements through slits having different positions relative to the openings of the caps.

7. A tooth shade comparator in accordance with claim 1, wherein said opposite end of said tube has an eyepiece with a magnifying lens therein, and wherein said eyepiece is adjustable on said tube for focusing of said lens relative to the patient's tooth and the shade guide element.

8. A tooth shade comparator in accordance with claim 1, wherein said light source comprises a tubular arm extending outwardly from said viewing tube and containing an electric lamp.

9. A tooth shade comparator in accordance with claim 8, wherein said lamp is a halogen lamp.

10. A tooth shade comparator in accordance with claim 1, further comprising color filter means insertable in a light path between said shade guide element and said opposite end of said tube.

11. A tooth shade comparator in accordance with claim 10, wherein said tube has a slot in a side wall thereof through which said filter means is inserted.

12. A tooth shade comparator in accordance with claim 1, wherein said means for receiving said shade guide element comprises a slit in a sidewall of said base.

13. A method of comparing color of a tooth in a patient's mouth with color of a shade guide element, comprising placing one end of a viewing tube over said tooth in a manner that substantially excludes ambient light from said tooth while exposing said tooth to the interior of said tube, placing said shade guide element adjacent to said tooth in a manner that substantially excludes ambient light from the shade guide element, illuminating said tooth and said shade guide element internally of said tube, and viewing said tooth and said shade guide element through said tube from an opposite end thereof.

14. A method in accordance with claim 13, further comprising substituting for said shade guide element another shade guide element having a color different from the first-mentioned shade guide element.

15. A method in accordance with claim 13, further comprising placing a filter in a light path between said shade guide element and said opposite end of said tube.

16. A method in accordance with claim 13, wherein said viewing comprises providing a magnified optical image of said tooth and said shade guide element.

17. A method in accordance with claim 13, wherein said illuminating comprises illuminating said tooth and said shade guide element through an opening in a side wall of said viewing tube.

18. A method in accordance with claim 13, wherein, prior to placing said one end of said viewing tube over said tooth, a removable base provided with an opening for exposing said tooth to the interior of said viewing tube is mounted on said one end of said viewing tube.

19. A method in accordance with claim 18, wherein said placing of said shade guide element adjacent to said tooth includes inserting said shade guide element through a slit in said base.

* * * * *